United States Patent
Ryan et al.

(10) Patent No.: US 6,576,009 B2
(45) Date of Patent: **\*Jun. 10, 2003**

(54) BIFURCATED INTRALUMINAL PROSTHESES CONSTRUCTION AND METHODS

(75) Inventors: Timothy J. Ryan, Los Gatos, CA (US); Michael A. Evans, Palo Alto, CA (US); Jay A. Lenker, Los Altos Hills, CA (US); Kirsten Freislinger, Menlo Park, CA (US); Steven W. Kim, Sunnyvale, CA (US); Allan R. Will, Atherton, CA (US)

(73) Assignee: Medtronic AVE, Inc., Santa Rosa, CA (US)

(\*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 8 days.

(21) Appl. No.: 09/502,942

(22) Filed: Feb. 11, 2000

(65) Prior Publication Data

US 2002/0156521 A1 Oct. 24, 2002

Related U.S. Application Data

(63) Continuation of application No. 08/704,960, filed on Aug. 29, 1996, now abandoned.
(60) Provisional application No. 60/008,254, filed on Dec. 1, 1995.

(51) Int. Cl.$^7$ .................................................. A61F 2/06
(52) U.S. Cl. ...................................... 623/1.35; 623/1.27
(58) Field of Search ........................... 623/1.16, 1.15, 623/1.27, 1.35

(56) References Cited

U.S. PATENT DOCUMENTS 3,945,052 A    3/1976   Liebig
4,503,569 A    3/1985   Dotter
4,512,338 A    4/1985   Balko et al.

(List continued on next page.)

FOREIGN PATENT DOCUMENTS

| EP | 0 357 003 A2 | 3/1990 |
| EP | 0 421 729 B1 | 4/1991 |
| EP | 0 472 731 A1 | 3/1992 |

(List continued on next page.)

OTHER PUBLICATIONS

Chuter et al., "Anatomy of the Infrarenal Aortic Aneurysm," Endoluminal Vascular Prosthese, pp. 21–36; Little Brown and Company; Boston (1995).
Donayre, et al., "Patient Selection and Preoperative Assessment," Endoluminal Vascular Prostheses, pp. 255–283; Little Brown and Company (1995).
World Medical Manufacturing Corporation Internet WEB Page Information, downloaded Aug. 4, 1997.
White et al., "Intravascular Stents," *A Color Atlas of Endovascular Surgery* pp. 83–87; J.B. Lippencott Company; Philadelphia (1990).

*Primary Examiner*—Bruce Snow
(74) *Attorney, Agent, or Firm*—Sterne, Kessler, Goldstein & Fox PLLC

(57) ABSTRACT

The present invention provides modular bifurcated intraluminal tubular prostheses, particularly stents and stent-grafts, for the treatment of disease conditions, particularly aneurysms. Modular sections of the prostheses, or "prosthetic modules," may be selectively assembled to form a prosthesis having characteristics which are tailored to the specific requirements of the patient, including branch angle and branch lumen sizes which match the patients vascular geometry. A Y-connector prosthetic module structure provides support and separation for each of the adjacent branching lumens. Radiopaque markers on the prostheses promote alignment between prosthetic modules and with the body lumen system.

54 Claims, 13 Drawing Sheets

U.S. PATENT DOCUMENTS

| | | |
|---|---|---|
| 4,550,447 A | 11/1985 | Seiler, Jr. et al. |
| 4,647,416 A | 3/1987 | Seiler, Jr. et al. |
| 4,718,907 A | 1/1988 | Karwoski et al. |
| 4,728,328 A | 3/1988 | Hughes et al. |
| 4,774,949 A | 10/1988 | Fogarty |
| 4,820,298 A | 4/1989 | Leveen et al. |
| 4,957,508 A | 9/1990 | Kaneko et al. |
| 5,019,090 A | 5/1991 | Pinchuk |
| 5,035,706 A | 7/1991 | Giantureo et al. |
| 5,064,435 A | 11/1991 | Porter |
| 5,078,726 A | 1/1992 | Kreamer |
| 5,151,105 A | 9/1992 | Kwan-Gett |
| 5,163,958 A | 11/1992 | Pinchuk |
| 5,211,658 A | 5/1993 | Clouse |
| 5,219,355 A | 6/1993 | Parodi et al. |
| 5,226,913 A | 7/1993 | Pinchuk |
| 5,229,045 A | 7/1993 | Soldani |
| 5,282,824 A | 2/1994 | Gianturco |
| 5,282,847 A | 2/1994 | Trescony et al. |
| 5,316,023 A | 5/1994 | Palmaz et al. |
| 5,330,500 A | 7/1994 | Song |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,383,928 A | 1/1995 | Scott et al. |
| 5,387,621 A | 2/1995 | Soldani |
| 5,397,345 A | 3/1995 | Lazarus |
| 5,405,377 A | 4/1995 | Cragg |
| 5,425,765 A | 6/1995 | Tiefenbrun et al. |
| 5,425,767 A | 6/1995 | Steininger et al. |
| 5,443,496 A | 8/1995 | Schwartz et al. |
| 5,443,499 A | 8/1995 | Schmitt |
| 5,456,713 A | 10/1995 | Chuter |
| 5,476,506 A | 12/1995 | Lunn |
| 5,507,767 A | 4/1996 | Maeda et al. |
| 5,507,769 A | 4/1996 | Marin et al. |
| 5,507,771 A | 4/1996 | Gianturco |
| 5,514,178 A | 5/1996 | Torchio |
| 5,545,210 A | 8/1996 | Hess et al. |
| 5,545,220 A | 8/1996 | Andrews et al. |
| 5,556,426 A | 9/1996 | Popadiuk et al. |
| 5,562,724 A | 10/1996 | Vorwerk et al. |
| 5,584,885 A | 12/1996 | Seckel |
| 5,591,229 A | 1/1997 | Parodi |
| 5,609,627 A | 3/1997 | Goicoechea et al. |
| 5,617,878 A | 4/1997 | Taheri |
| 5,618,301 A | 4/1997 | Hauenstein et al. |
| 5,628,783 A | 5/1997 | Quiachon et al. |
| 5,632,763 A | 5/1997 | Glastra |
| 5,632,772 A | 5/1997 | Alcime et al. |
| 5,639,278 A | 6/1997 | Dereume et al. |
| 5,653,743 A | 8/1997 | Martin |
| 5,653,747 A | 8/1997 | Dereume |
| 5,662,675 A | 9/1997 | Polanskyj Stockert et al. |
| 5,676,697 A | 10/1997 | McDonald |
| 5,693,088 A | 12/1997 | Lazarus |
| 5,716,410 A | 2/1998 | Wang et al. |
| 5,723,004 A | 3/1998 | Dereume et al. |
| 5,733,325 A | 3/1998 | Robinson et al. |
| 5,735,290 A | 4/1998 | Sterman et al. |
| 5,769,885 A | 6/1998 | Quiachon et al. |

FOREIGN PATENT DOCUMENTS

| | | |
|---|---|---|
| EP | 0 506 918 B1 | 10/1992 |
| EP | 0 508 473 A2 | 10/1992 |
| EP | 0 551 179 A1 | 7/1993 |
| EP | 0 646 365 A1 | 4/1995 |
| EP | 0 684 022 A2 | 11/1995 |
| EP | 0 686 379 | 12/1995 |
| EP | 0 689 805 A2 | 1/1996 |
| EP | 0 722 701 A1 | 7/1996 |
| FR | 2 678 508 | 1/1993 |
| SU | 1 457 921 | 2/1989 |
| WO | WO 95/05132 | 2/1995 |
| WO | WO 95/08966 | 4/1995 |
| WO | WO 95/09586 | 4/1995 |
| WO | WO 95/16406 | 6/1995 |
| WO | WO 95/18585 | 7/1995 |
| WO | WO 95/23563 | 9/1995 |
| WO | WO 95/26695 | 10/1995 |
| WO | WO 95/29646 | 11/1995 |
| WO | WO 95/32688 | 12/1995 |
| WO | WO 95/34255 | 12/1995 |
| WO | WO 96/00103 | 1/1996 |
| WO | WO 96/03092 | 2/1996 |
| WO | WO 96/23455 | 8/1996 |
| WO | WO 97/07751 | 3/1997 |

BIFURCATED INTRALUMINAL PROSTHESES CONSTRUCTION AND METHODS

This application is a continuation of application Ser. No. 08/704,960 filed Aug. 29, 1996, now abandoned, which claims priority of U.S. Provisional Application Serial No. 60/008,254 filed Dec. 1, 1995.

BACKGROUND OF THE INVENTION

1. Field of the Invention

The present invention relates generally to endoluminal tubular prostheses, such as stents, stent-grafts, and other structures. More particularly, the present invention provides bifurcated prosthesis structures having properties which are tailored for individual body lumens, including blood vessels, particularly for the treatment of abdominal and other aneurysms.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 2% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular prosthesis placement for the treatment of aneurysms has been proposed. Although very promising, many of the proposed methods and apparatus suffer from undesirable limitations. In particular, proper sizing of endovascular prostheses can be problematic.

Proper matching of the prosthesis to the branching blood vessel is critical to the treatment of an aneurysm. The prosthesis preferably extends axially beyond the weakened portion of the blood vessel to anchor securely in the healthy vessel wall. However, the cross-sectional size and axial length of individual blood vessels vary considerably between patients. Even within a patient, the cross-section and resilience of a lumen wall can vary considerably along its axial length, and the location and extent of the aneurysm will differ with different patients. Additionally, each prosthesis must be carefully constructed and handled, making it extremely costly to provide and maintain the large selection of prostheses required for proper fitting of every individual patient.

Known branching intraluminal prostheses are generally formed as tubular, radially-expandable stent-grafts. These stent-graft structures have typically been formed with simplistic cylindrical frames or "stents". A separate liner or "graft" is typically attached to the frame to prevent blood flow through a ruptured vessel wall. Such liners are often formed from inelastic textiles to prevent pressure from distending a weakened luminal wall. These branching textile liners have often been woven as continuous branching tubes to avoid any seams or joints which might fail after the stent-graft has been positioned. Unfortunately, this has also resulted in branch perimeters which are each a fraction of the perimeter of the liner at the common lumen, each branch typically being half the common lumen in diameter. This does not accurately reflect the relative sizes of branching body lumens. Hence, some mismatch are inevitable when using the proportional branching stent-grafts of the prior art.

Another problem associated with the branch stent-grafts of the prior art is that these known cylindrical structures generally form parallel branches when at rest, while the branches of body lumens often separate at significant branching angles. Although it is possible to deform a straight branching prosthesis, the imposition of such axial bends on endovascular stent-grafts tends to cause folding and/or wrinkling which occlude their lumens and degrade their therapeutic value.

Still another disadvantage of known bifurcated stent-grafts is that they often result in an imbalance in flow area to the different branches. Existing stent-grafts often rely, for at least some distance, solely on the liner material to maintain separation between branching lumens. Such an external frame structure to support an internal flexible liner, although effective at holding the total liner lumen open, does not provide a fixed separation between lumens. Instead, the liner material often pushes over to one side or the other. Although it is possible to separate the lumens with a portion of the frame, compression of such dual lumen frames is problematic, and would increase the total compressed diameter of branching prostheses.

For these reasons, it would be desirable to provide improved branching endoluminal prostheses, including stents and stent-grafts, and improved methods for placement of such endoluminal prostheses to treat aneurysms and other conditions. It would further be desirable to provide endoluminal prostheses which match the actual luminal geometries of blood vessels and other body lumens without compromising their therapeutic effectiveness. It would be particularly desirable to provide adaptable prostheses and methods for their replacement which would facilitate effective treatment of widely varying luminal system geometries without requiring an excessive inventory of prostheses to choose from.

2. Description of the Background Art

Copending U.S. patent application Ser. No. 08/538,706 (Attorney Docket No. 16380-38), the full disclosure of which is hereby incorporated by reference, describes modular prostheses and constructions methods which are particularly advantageous for use with the bifurcated prostheses of the present invention.

U.S. Pat. No. 5,064,435 describes a self expanding prosthesis which maintains a stable axial length during expansion by anchoring of radially outward flares at each end, and by sliding of an overlapping medial region therebetween.

Vascular grafts and devices for their endoluminal placement are described in U.S. Pat. Nos. 5,282,824; 5,272,971; 5,242,399; 5,219,355; 5,211,658; 5,201,757; 5,192,297; 5,190,058; 5,158,548; 5,147,370; 5,104,399; 5,092,877; 5,078,726; 5,019,085; 4,990,151; 4,950,227; 4,913,141;

4,886,062; 4,820,298; 4,787,899; 4,617,932; 4,562,596; 4,577,631; and 4,140,126; and European Patent Publications 539,237; 533,511; 518,839; 518,704; 508 473; 505,686; 466 518; and 461 791. Catheters for placing vascular stents are described in U.S. Pat. Nos. 5,192,297; 5,092,877; 5,089,005; 5,037,427; 4,969,890; and 4,886,062. Catheters carding a graft structure in a tube or capsule are described in U.S. Pat. Nos. 5,275,622; 5,104,399; and 4,787,899; and EP466518.

SUMMARY OF THE INVENTION

The present invention provides branching modular intraluminal tubular prostheses, particularly stents and stent-grafts, for the treatment of disease conditions, particularly aneurysms. Modular sections of the branching prostheses, or "prosthetic modules," may be selectively combined to assemble a prosthesis having characteristics which are tailored to the specific requirements of the patient. Each prosthetic module preferably includes one or more standard interface ends for engaging another module, the module/module interface typically comprising ends which overlap and/or lock within a predetermined axial range. Advantageously, the axial length, cross-section, perimeter, resilient expansive force, axial flexibility, liner permeability, liner extensibility, radial conformability, liner/tubal wall sealing and anchoring, and other prosthetic characteristics may be varied along the axis of the assembled prosthesis, and also along the axis of each prosthetic module. The modules are preferably individually introduced into a lumen system of a patient body so that the prosthesis is assembled in situ. Ideally, selection of appropriate prosthetic modules and the flexibility of the interface overlap range provides a custom fit intraluminal prosthesis which provides a therapy tailored to the individual patient's needs.

The present invention provides endoluminal prosthetic structures and methods which are particularly advantageous when applied within modular prosthetic therapies of the vascular system. Additionally, several aspects of the present invention will find use during other endoluminal prosthetic procedures. Thus, intraluminal prostheses of the present invention are suitable for a wide variety of therapeutic uses, including stenting of the ureter, urethra, biliary tract, and the like. The present devices and methods will also be useful for the creation of temporary or long term lumens, such as the formation of fistulas. The present invention will find its greatest use, however, in the placement of endovascular prostheses into blood vessels for the treatment of abdominal and other aneurysms, vascular stenoses, and the like.

In a first aspect, the present invention provides a branching endoluminal stent-graft comprising a flexible liner over which a radially expandable frame is disposed. The flexible liner has a main body with a common lumen, and first and second branches having first and second branch lumens, the first and second branch lumens being in communication with the common lumen. When expanded, the frame defines a cross-section having a first lobe supporting the first branch and a second lobe supporting the second branch, and an isthmus therebetween.

Generally, two roughly opposed indentations are between the first and second lobes, and an attachment mechanism attaches the first lobe and a portion of each indentation to the first branch. Similarly, the attachment mechanism also attaches the second lobe and an alternate portion of each indentation to the second branch. Thus, both the lobes and indentations help to support the liner lumens in an open configuration when the frame is expanded, while the indentation also provide separation between the lumens. As the frame cross-section is generally contiguous, the frame itself having only a single structural lumen, radial compression of the frame to a small diameter for insertion and positioning within the body lumen system is not compromised.

In another aspect, the present invention provides a branching endoluminal stent-graft comprising a radially expandable tubular frame and a flexible inelastic liner supported by the frame. The liner has a main body with a common lumen, and first and second branches extending from the body having first and second branch lumens, respectively. These first and second branch lumens are in communication with the common lumen, and a perimeter of the common lumen is smaller than a sum of the perimeter of the first branch lumen and a perimeter of the second branch lumen. Preferably, the sum of the first and second branch lumen perimeters is between 1% and 20% more than the common lumen perimeter. This structure promotes anatomical matching of the prosthesis with branching body lumen systems, particularly with the abdominal aorta and iliac arteries for the treatment of abdominal aneurysms. Advantageously, the liner often comprises a continuously woven tube to avoid the dangers associated with seams or the like. Conveniently, the liner may be selectively shrunk, or may alternatively be plastically expanded, to provide the anatomically matched perimeters of the present invention.

In yet another aspect, the present invention provides an angled branch endoluminal prosthesis comprising a radially expandable tubular main body having a common lumen and a radially expandable tubular first branch extending from the main body. The first branch has a first branch lumen in fluid communication with the common lumen when the prosthesis is expanded. Similarly, a radially expandable tubular second branch extends from the main body, and has a second branch lumen in fluid communication with the common lumen when the prosthesis is expanded. The common lumen and the first branch lumen define a first open flow path having a preset first branch angle in the range between 15° and 90° when the prosthesis is expanded. Typically, the common lumen and the second branch lumen will also define a second open flow path having a preset second branch angle in the range between 15° and 90°. Preferably, the first and second branch angles will be in the range between 30° and 45°. These preset branch angles match the common branching angles of the iliac arteries from the abdominal aorta, thereby improving flow through prostheses used in the treatment of abdominal aneurysms.

Oftentimes, the angled branch prostheses of the present invention will comprise resilient structures which form the preset bend angle when at rest. Hence, once the prosthesis is implanted, axial bending of the prosthesis by the surrounding tissues is minimized, reducing wrinkling and folding of the lumen. Such a structure also avoids the imposition of straightening forces against weakened vessel tissues. In a particularly advantageous embodiment, the liner comprises a corrugated region to increase the local axial flexibility of the prosthesis, and to allow the prosthesis to adapt to a range of branch angles.

In another aspect, the present invention provides an angled prosthetic module comprising a radially expandable tubular body portion having a bend and a lumen. The lumen provides an open flow path when the bend defines a preset angle in the range between 15° and 90°. A standard interface is disposed on an end of the body portion, the standard interface fittingly engagable with any of a plurality of standard interface ends of other endoluminal prosthetic modules. Generally, the bend has a preset radial orientation and the prosthesis further comprises a rotational marker disposed on the body or interface end. Such rotational markers, typically being visible under fluoroscopy, greatly facilitate alignment of the preset radial orientation of the prosthesis with a bend in the body lumen.

In yet another aspect, the present invention provides an endoluminal prosthesis kit comprising an expandable tubular Y-connector module having a common lumen, a first branch lumen, and a second branch lumen, the first and second branch lumens being in communication with the common lumen. At least one of the common lumen, the first branch lumen, and the second branch lumen have an associated first standard interface end. A plurality of alternative radially expandable prosthetic modules are associated with each standard interface end. Each of the alternative modules has a tubular body portion and a second interface end. Each associated interface end is fittingly engagable with the first interface end, and the plurality of alternative body portions provide different selectable assembled prosthetic characteristics. Generally, the alternative body portions will differ in at least of length, cross-section, taper, bend angle, axial flexibility, exterior fiber protrusion, liner permeability, liner extensibility, radial conformability, or resilient radial spring force. In a particularly preferred embodiment, the first and second interface ends overlap within a predetermined range when engaged. This overlap range allows the total axial length of the assembled prosthesis to be tailored to the particular patient's needs.

In yet another aspect, the present invention provides an endoluminal prosthetic Y-connector module comprising a radially expandable body portion having a common lumen, a first branch lumen, and a second branch lumen, the first and second branch lumens being in communication with the common lumen. At least one standard interface end is disposed on the body portion adjacent to at least one of the common lumen, the first branch lumen, and the second branch lumen. Each standard interface end is fittingly engagable with any of an associated plurality of standard interface ends of other endoluminal prosthetic modules having differing prosthetic characteristics.

In yet another aspect, the present invention provides a marked stent-graft comprising a radially expandable tubular frame, a flexible liner supported by the frame, and an attachment mechanism which holds the liner on the frame. Markers are disposed on at least one of the frame, the liner, and the attachment mechanism. The markers are visible under imaging to indicate the axial and/or rotational position of the stent-graft.

As used herein, "visible under imaging" means an element which is visible under fluoroscopy, ultrasound, or other imaging modalities, so as to define an identifiable shape which is distinguishable from the adjacent structural elements and the surrounding body tissues. Preferably, the markers indicate position both while the prosthesis is in a compressed mode, as is typically used during insertion, and also while the prosthesis is in the expanded mode after it has been deployed. The marker thereby facilitate positioning of the prosthesis, and also allows continuing verification of the position of the deployed prosthesis relative to the body tissues. Finally, such markers may also be used to position additional prosthetic modules relative to the expanded prosthesis.

The present invention further provides a method for placement of stent-grafts comprising inserting a branching stent-graft into a patient body and positioning the branching stent-graft at a target location within a body lumen. The branching stent-graft comprises a tubular frame and a flexible liner having a main body with a common lumen. The stent-graft is expanded at the target location, and the liner is supported at a cross-section by the frame so that the common lumen is held in open. At a second cross-section, a first lobe of the frame holds a first lumen of the liner open, and a second lobe of the frame holds a second lumen of the liner open. An isthmus of the frame disposed between the first lobe and the second lobe separates the first lumen from the second lumen. This separation of the lumens is particularly beneficial when a tubular branch prosthesis is inserted into, and expanded within, either the first or second lumen, as it maintains the intended balance between the branching luminal flows.

In another aspect, the present invention provides a method for placement of a branching endoluminal stent-graft comprising inserting a branching stent-graft into a patient body, and positioning the branching stent-graft at a target location within a body lumen. The branching stent-graft is expanded at the target location, the branching stent-graft comprising a tubular frame and an inelastic liner. The liner is held in an open configuration by the frame so that a perimeter of a common lumen of the liner is smaller than a sum of a perimeter of a first branch lumen of the liner and a perimeter of a second branch lumen of the liner, thereby anatomically matching branching body lumen geometries.

In yet another aspect, the present invention provides a method for treating a bent target region of a body lumen, the method comprising inserting an endoluminal prosthesis into the body lumen in a radially compressed configuration. The prosthesis has a bend defining a preset angle when in an expanded configuration. The prosthesis is positioned at the bent target region, and the preset angle is rotationally aligned with the bent target region. The aligned prosthesis is then expanded at the bent target region, thereby avoiding any kinking or wrinkling of the prosthesis lumen, and avoiding straightening loads imposed by the prosthesis on the surrounding body lumen.

In yet another aspect, the present invention provides a method of producing a branching stent-graft comprising providing a flexible tubular liner having a main body, a first branch extending from the main body, and a second branch extending from the main body. At least a portion of the main body is selectively shrunk relative to at least one of the first branch and the second branch. A radially compressible frame is attached to the tubular liner. Typically, a perimeter of the main body portion is shrunk by up to 20% relative to a perimeter of at least one of the first branch and the second branch.

In yet another aspect, the present invention provides a method for producing a branching endoluminal prosthesis, the method comprising fabricating a resilient tubular frame and expanding the frame to an expanded configuration. The expanded frame is then heat-treated while being restrained with a cross-section that defines two lobes separated by at least one indentation. A flexible liner is attached to a first lobe and an adjacent portion of the at least one indentation, so that a first lumen of the liner is held open by the frame.

In yet another aspect, the present invention provides a modular endoluminal prosthesis placement method comprising inserting a Y-connector prosthetic module within a body lumen system, and positioning a main body of the Y-connector prosthetic module at a target location adjacent to first and second branch lumens of a body lumen system. The first prosthetic module is radially expanded at the target location. A preferred first branch prosthetic module is selected from a plurality of alternative branch prosthetic modules, and an end of the preferred first branch prosthetic module is positioned adjacent to the first branch of the body lumen system. The preferred first branch prosthetic module is radially expanded, and once expanded, engages the Y-connector prosthetic module.

In yet another aspect, the present invention provides a method for assembling endoluminal prosthetic modules within a body lumen, the method comprising deploying a first prosthetic module within the body lumen, and inserting a second tubular prosthetic module into the body lumen in a radially compressed configuration. Markings disposed on at least one of the first and second prosthetic module are imaged, and an image of the markings is aligned with an image of the other of the first prosthetic module and the second prosthetic module. An end of the aligned second prosthetic module is then expanded to engage an end of the first prosthetic module.

In a final aspect, the present invention provides a method for positioning endoluminal prosthetic modules within a body lumen, the method comprising inserting a tubular prosthesis into the body lumen in a radially compressed configuration. Markings disposed upon the inserted prosthetic module are imaged, and an asymmetric marker element is rotationally oriented, thereby providing a rough rotational alignment of the prosthesis. The image of marker elements disposed at different radial locations about the prosthesis may then be brought together to precisely rotationally align the prosthesis within the body lumen. Finally, the aligned prosthesis may then be expanded within the body lumen.

DESCRIPTION OF THE SPECIFIC EMBODIMENTS

The present invention will find its greatest use as an endovascular prostheses for the treatment of diseases of the vasculature, particularly aneurysms, stenoses, and the like. The prostheses will generally be radially expandable from a narrow-diameter configuration to facilitate introduction into the body lumen, typically during surgical cutdown or percutaneous introduction procedures. Exemplary delivery catheters and methods for placement of the prostheses of the present invention are more fully described in copending U.S. patent application Ser. No. 08/475,200, (Attorney Docket No. 16380-11-3), the full disclosure of which is incorporated herein by reference.

Figure 1:
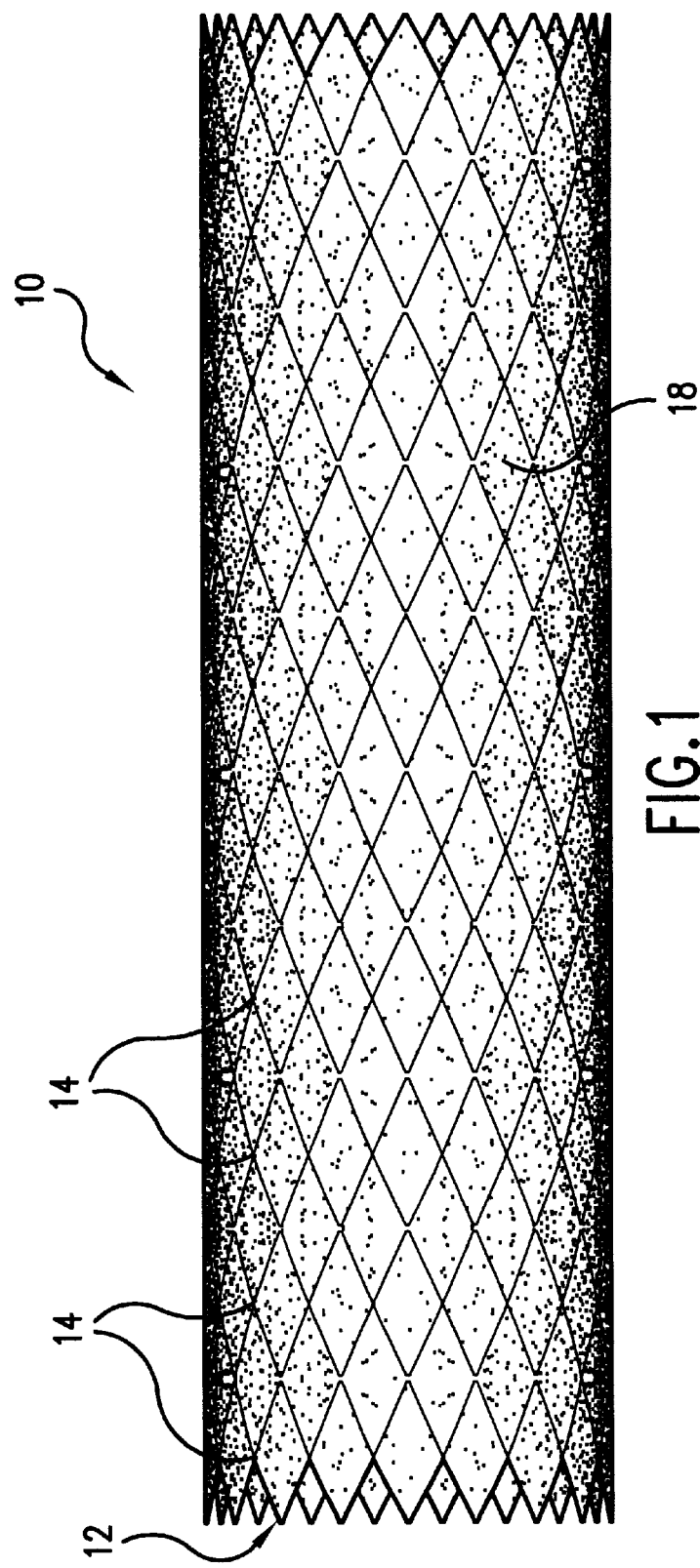
FIG. 1 is a side view of an exemplary cylindrical vascular graft having axially constant characteristics.

An exemplary cylindrical graft structure 10 is illustrated in FIG. 1. Prosthesis 10 comprises a perforate tubular frame 12 which includes a plurality of independent (non-connected) ring frames 14. The tubular frame 12 supports an inner liner 18. Optionally, an outer liner is disposed over the ring frames, either instead of inner liner 18, or in combination therewith.

To secure ring frames 14 in place, and to secure the liner to the perforate tubular frame 12, the liner is typically sutured to the frame. A wide variety of alternative liner/frame attachment mechanisms are available, including adhesive bonding, heat welding, ultrasonic welding, and the like. Where inner and outer liners are used, the ring frames may be sandwiched between the liners and held in place by attaching the liners to each other.

The prosthesis 10 will typically have a length in the range from about 20 mm to 500 mm, preferably from 50 mm to 200 mm, with a relaxed diameter in the range from about 4 mm to 45 mm, preferably being in the range from 5 mm to 38 mm.

Figure 2:
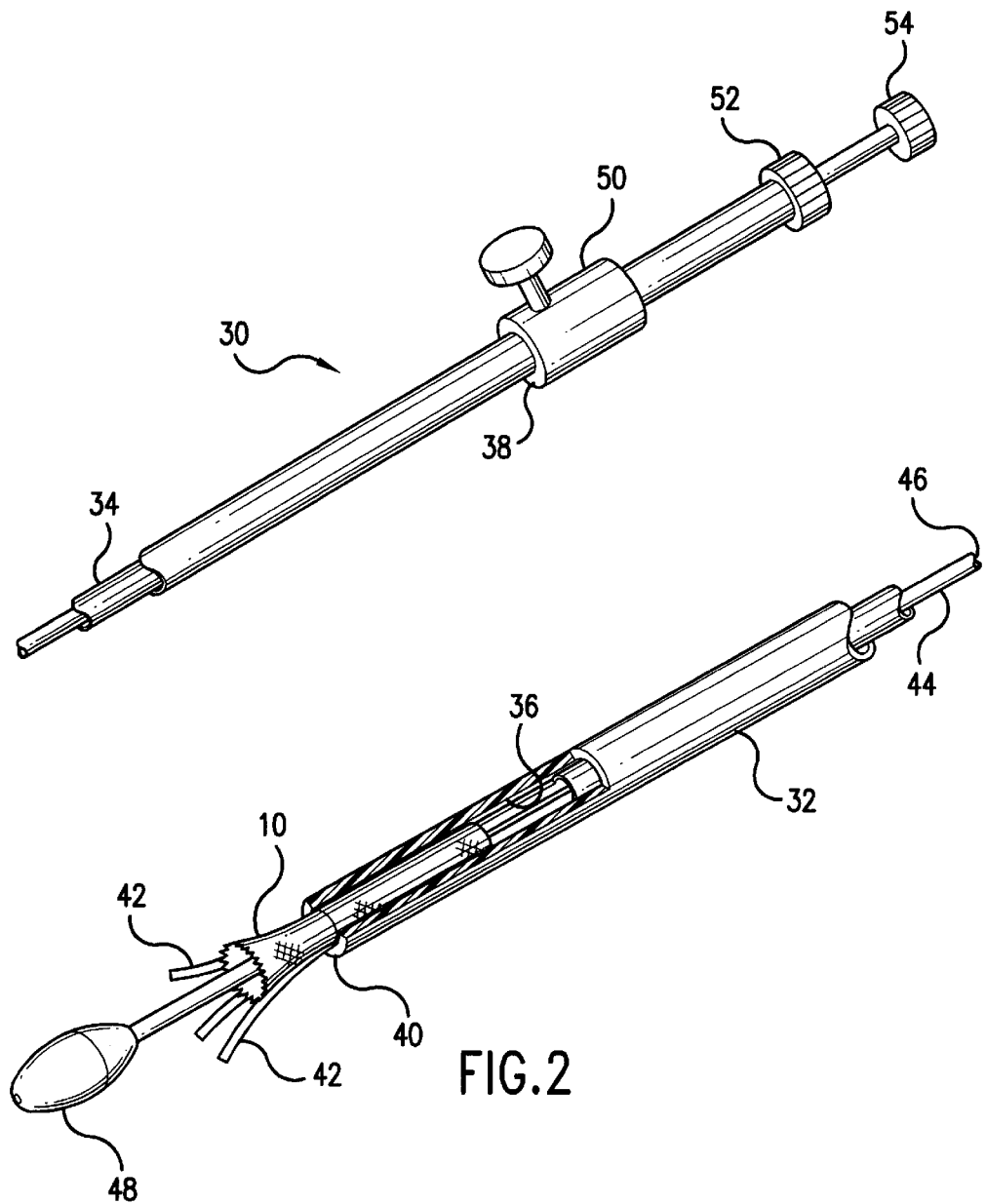
FIG. 2 is a perspective view of an exemplary delivery catheter for use with the prostheses of the present invention, with a portion of the distal end broken away to disclose a prosthesis therein.

Referring now to FIG. 2, an exemplary delivery catheter 30 for use with the endoluminal prostheses of the present invention comprises a tubular cover 32 and a shaft 34. Cover 32 has a central lumen 36 extending from a proximal end 38 to a distal end 40. Shaft 34 is slidably received within central lumen 36 and extends proximally of cover 32.

A plurality of runners 42 extend distally from shaft 34. Runners 42 line a portion of the inner surface of lumen 36, and slide within the lumen with the shaft. Shaft 34 also has a lumen, in which a core shaft 44 is slidably disposed. Core shaft 44 has a guide wire lumen 46. Nosecone 48 is fixed to the distal end of core shaft 44, and can therefore be manipulated independently of runners 42.

Prosthesis 10 is radially compressed and restrained within the plurality of runners 42. In turn, cover 32 prevents runners 42 from expanding outward. Runners 42 are formed from a hard material, and distribute the expansion load of prosthesis 10 over the inner surface of central lumen 36. The deploying force is applied proximally against a slider 50 attached to distal end 38 of cover 30, while holding a luer fitting 52 at the distal end of shaft 34, thereby withdrawing the cover proximally from over the prosthesis. An additional luer adaptor 54 at the distal end of core shaft 44 allows the core shaft to be manipulated independently, and to be releasably secured to the shaft 34.

Figure 3:
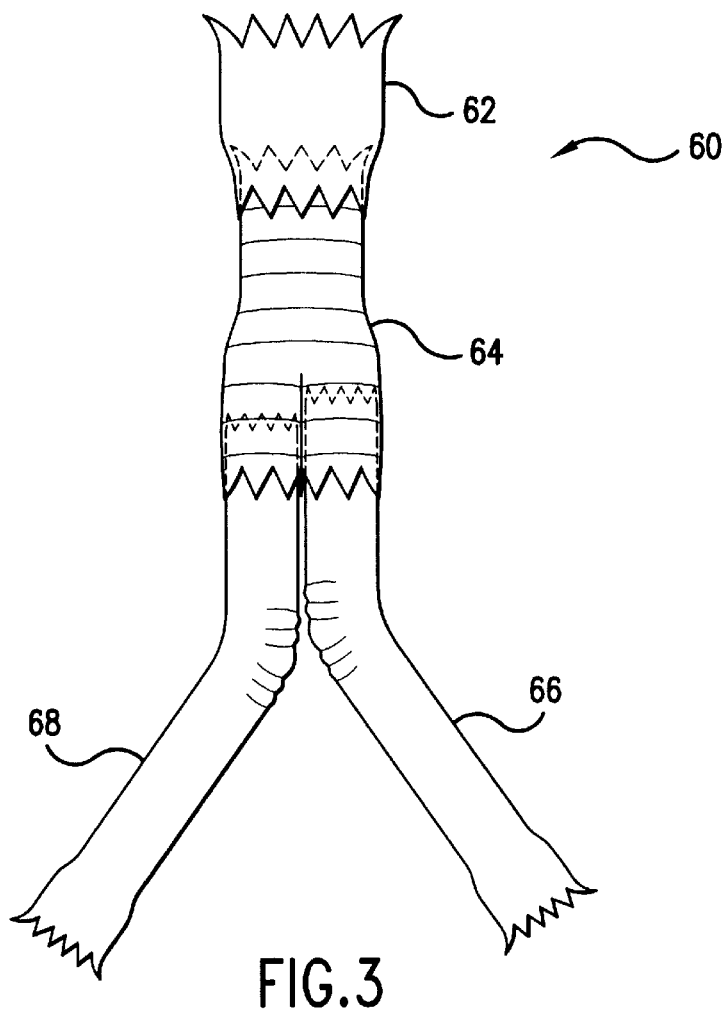
FIGS. 3 and 3A illustrate a branching endoluminal prosthesis assembled from a plurality of prosthetic modules according to the principles of the present invention.
Figure 3A:
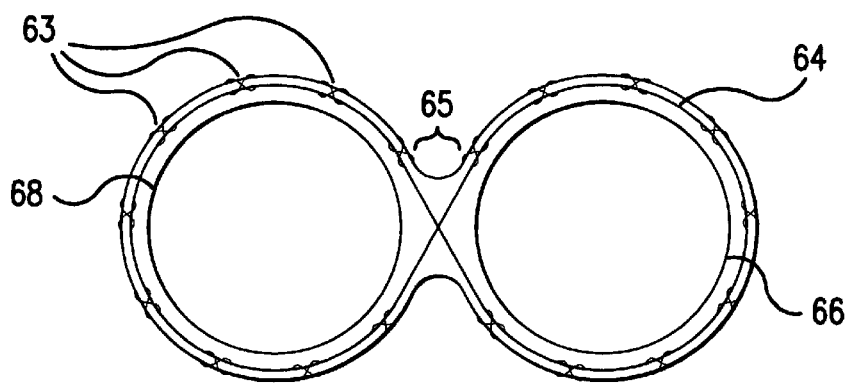

Referring now to FIGS. 3 and 3A, a branching endoluminal stent-graft 60 is assembled from prosthetic modules selected to match the needs of the diseased vascular system of the patient. A common lumen cuffed prosthetic module 62 seals and anchors the assembled prosthesis in the body lumen, typically within the abdominal aorta below the renal arteries and above the left and right iliac arteries. Y-connector module 64 engages cuffed common lumen module 62, and separates the blood flow for the iliac arteries. First angled branching prosthetic module 66 and second angled branching prosthetic module 68 engage the branch lumens of Y-connector module 64 to direct the luminal flow along first and second branching body lumens.

The modular construction of branching prosthesis 60 allows individual tailoring of the common lumen, first branch lumen, and second branch lumen to match the geometry of the body lumen system. For example, a perimeter of common lumen cuffed module 62 may be selected independently of the branching lumen perimeters. Specifically, the perimeter of the abdominal aorta is typically as much as 20% less than the sum of the perimeters of the iliac arteries. Preferably, these relative luminal proportions are reflected in Y-connector module 64, ideally by selective shrinking of a flexible liner, wherein the Y-connector comprises a stent-graft. Selective shrinking of stent-graft liners is fully explained in copending U.S. patent application Ser. No. 08/538,706 (Attorney Docket 16380-38), the full disclosure of which has previously been incorporated herein by reference.

The cross-sectional shape of Y-connector module 64 is particularly advantageous for use in the modular endoluminal protheses of the present invention. The cross-section adjacent the branches includes individual lobes which receive the first and second branch modules 66, 68, and also includes an isthmus 65 between these lobes to maintain a fixed separation between the branches, such that the Y-connect module 64 has an uninterrupted cross-section over its entire length. Additionally, as illustrated in FIG. 3C and described hereinbelow, the lobes and indentations defining isthmus 65 increases the area available for suture 63 or other frame/liner attachment mechanisms.

Figure 4:
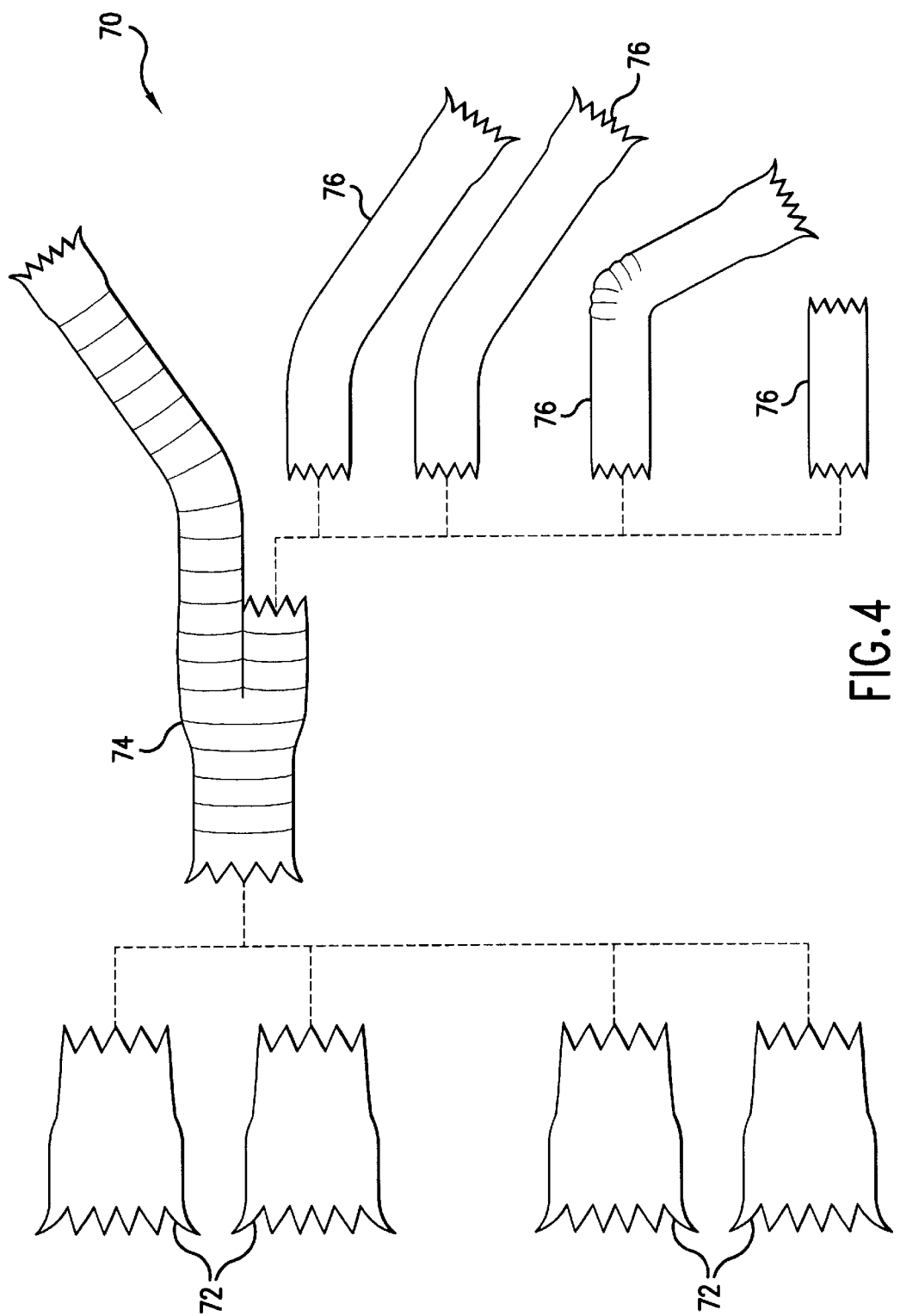
FIG. 4 is a schematic illustration of a modular branching prosthesis kit, according to the principles of the present invention.

Referring now to FIG. 4, a branching endoluminal prosthesis kit 70 includes a plurality of alternative selectable common lumen modules 72 which vary in diameter, length, or other prosthetic characteristics. Each of common lumen modules 72 interchangeably engages branching module 74. Branching module 74 comprises a Y-connector module having a single extended branch, thereby minimizing the number of joints and the prosthesis positioning and assembly time, while still allowing variability between the two branches and the common lumen end. A plurality of second branch prosthetic modules 76 provide variations in diameter, length, preset bending angle, and the like. These second branch prosthetic modules may optionally include cuffed ends, or may alternatively be engagable by still further prosthetic modules.

A particularly advantageous structure for use in a branching endoluminal Y-connector will be described with reference to FIG. 5. Y-connector module 64 comprises a radially expandable frame 80 supporting a liner 82. Frame 80, in turn, comprises a plurality of ring frames 78 which are interconnected by bridges 84. Frame 80 therefore forms a fairly stiff structure, particularly when liner 82 is attached to a malleable frame. Alternatively, frame 80 may be formed as a series of independent, frame rings to increase the axial flexibility of the Y-connector module. Such independent frame rings may be resilient, malleable, or both.

Figure 5D:
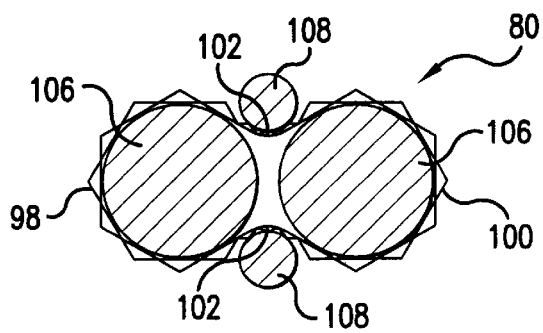
FIG. 5D illustrates a method for producing the lobed cross-section of the Y-connector prosthetic module of FIG. 5.
Figure 5:
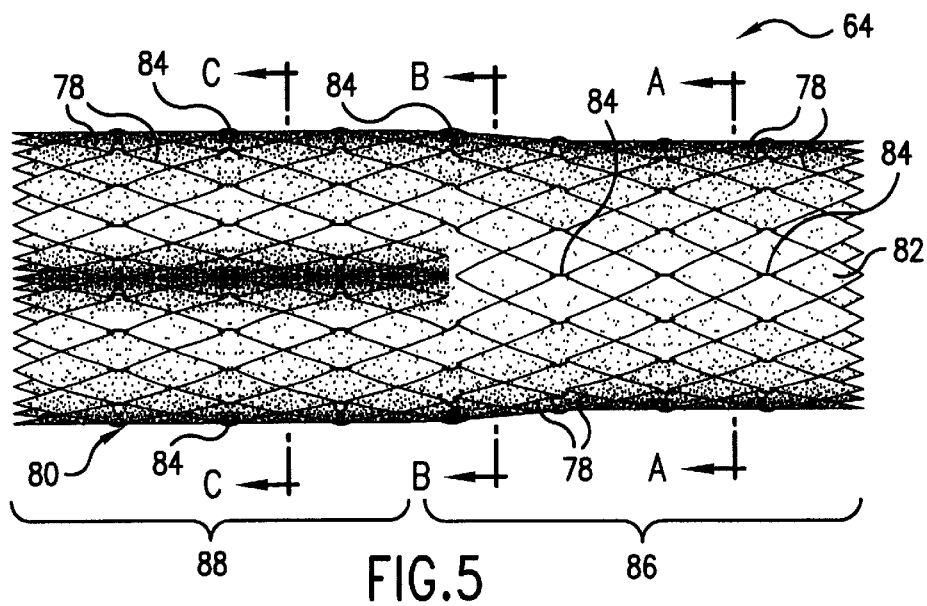
FIG. 5 illustrates a preferred prosthetic Y-connector module structure having a branching flexible liner which is supported by a radially expandable frame including two lobes separated by opposed indentations, for use with the modular prothesis kit of FIG. 4.

Liner 82 of Y-connector module 64 includes a main body 86 and a septum 88. As is seen most clearly in FIGS. 5A–C, the liner along main body 86 defines a single common lumen 90. Along septum 88, the liner defines a first branch lumen 92 and a second branch lumen 94. The first and second branch lumens 92, 94 may be entirely separate, but are preferably interconnected along center line 96 to help hold the liner in an open configuration. The liner is preferably formed as a continuous woven tube, thereby avoiding seams and/or joints which might fail after placement. Ideally, the liner comprises a woven polyester such Dacron™, which has been selectively shrunk to match the anatomical lumen geometries.

Figure 5C:
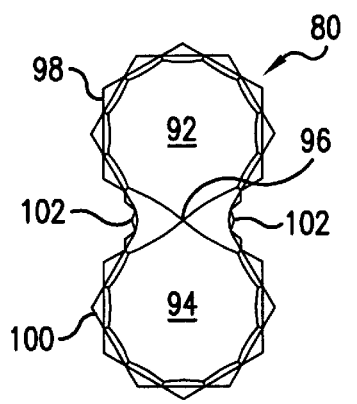
FIGS. 5A–C illustrate cross-sections along the axis of the Y-connector prosthetic module of FIG. 5.
Figure 5B:
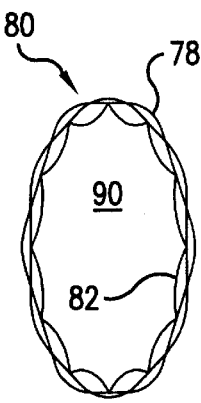
Figure 5A:
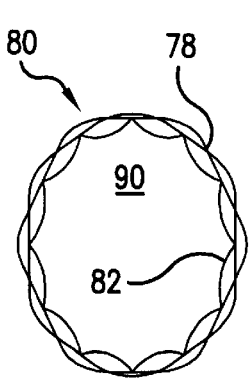

As is most clearly seen in FIG. 5C, a cross-section of frame 80 adjacent to the septum of the liner defines a contiguous cross-section having a first lobe 98, a second lobe 100, and opposed indentations 102 to support and separate the first and second branches of the liner. The contiguous nature of the frame facilitates compression of the frame by avoiding frame internal crossing elements, while the lobes and indentations increase the attachment area between each liner branch and its associated portion of the frame.

The lobes and indentations further ensure that the flow between the two branches will remain even by substantially separating the septum of the liner into distinct flow areas. This is particularly important where prosthetic branch modules will be inserted into the septum, as the expansion of such branch modules within the septum would tend to push an unsupported liner to one side, resulting in an uneven flow. This interaction can be understood with reference to FIG. 3, where first branch module 66 has been inserted farther into the septum than second branch module 68. If the flexible liner alone were relied upon to maintain distribution between the branches, the inserted end of first branch module 66 may well push the liner barrier into the flow region intended for the second branch of the body lumen.

Referring now to FIG. 5D, the preferred method for imposing the separated lobed cross-section on Y-connector frame 80 comprises supporting the frame on a jig having lobe dowels 106 and indentation dowels 108. While the frame is supported on the jig, the frame is heat-treated, resiliently biasing the frame toward the lobed cross-section. Typically, the frame will be formed from a biocompatible high-strength alloy such as stainless steel, platinum, or the like, ideally comprising a shape-memory alloy such as Nitinol™.

Although the preferred frame structure has been described with reference to a Y-connector module, thereby taking advantage of the modular prosthesis construction of the present invention, the lobed frame structure will be advantageous for any branching endoluminal stent-graft, as it maintains each lumen of the liner in an open configuration by supporting the liner along a greater proportion of its perimeter, but without compromising the radial compressibility of the total stent-graft.

Figure 6:
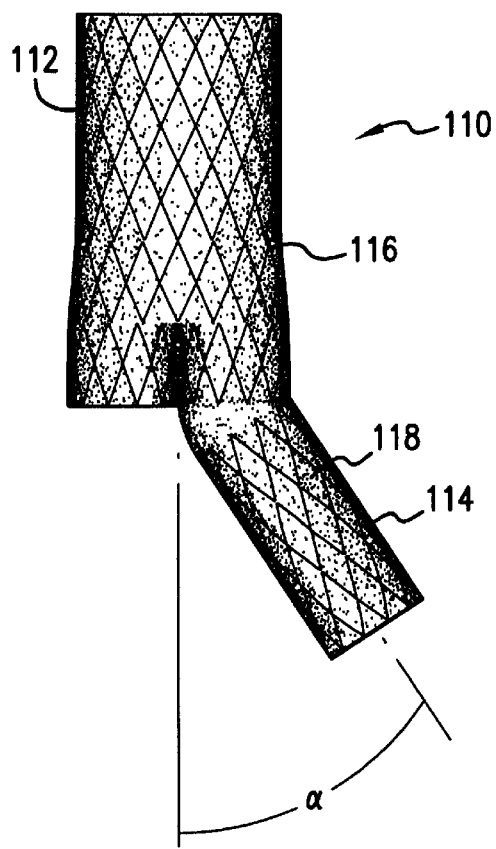
FIG. 6 illustrates an angled branch endoluminal prosthesis having a preset branch angle, according to the principles of the present invention.
Figure 6A:
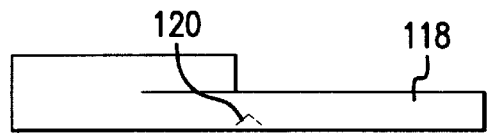
FIGS. 6A–B illustrate a method for producing a prebent liner for use in the angled branch prosthesis of FIG. 6.
Figure 6B:
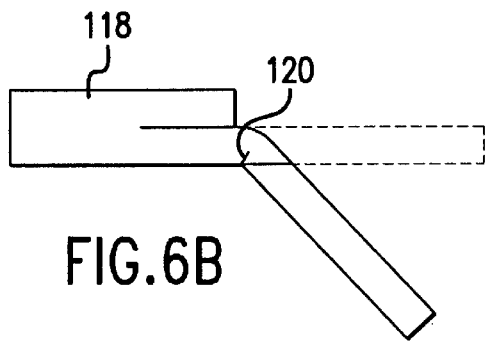

Referring now to FIGS. 6–6B, a preferred angled branch stent-graft 110 includes a common lumen 112 and a first branch 114 which forms a branch angle a relative to the common lumen portion 112 when the prosthesis is at rest. It has been found that the abdominal aorta and iliac arteries define angles of between 15° and 90°, more commonly between 30° and 45°. While the endoluminal prostheses of the prior art have been designed to allow some axial bending, imposition of such angles often leads to kinking and/or wrinkling of the liners of known endoluminal stent-grafts. The prostheses of the present invention are typically straightened and radially compressed during insertion, but will form the preset bend angle a when expanded and in a relaxed state.

While a frame 116 may be biased to form an angle α without a prebent liner, the open flow path through the bent prosthesis lumen is greatly improved by preforming liner 118 to accept the bent configuration. As illustrated in FIGS. 6A–B, prebent liner 118 may be formed simply by folding and stitching inner bend region 120. Optionally, the excess material may be removed. Although such a method is effective at setting a specific prebend angle α, the sharp bend in the branch lumen will still impede luminal flow somewhat, and wrinkling and/or kinking may result if there is a significant mismatch between the bend angle of the prosthesis and the bend angle of the body lumen.

Figure 6C:
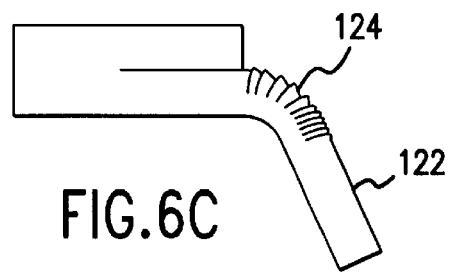
FIGS. 6C–E illustrate a corrugated liner having a preset branch angle, and which maintains an open flow path within a range of branch angles, for use in the angled branch endoluminal prosthesis of FIG. 6.
Figure 6D:
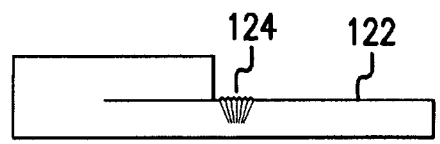
Figure 6E:
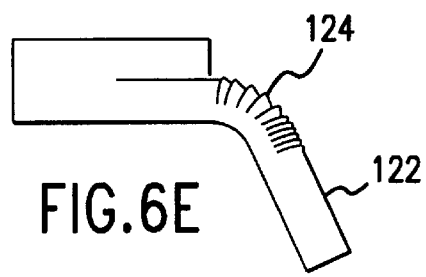

Referring now FIGS. 6C–E, a preferred prebent liner 122 includes a corrugated joint 124. Such a corrugated liner will typically also have a prebend angle, but will adapt to a much wider range of branch angles without excessively occluding the branch lumen flow. Formation of such a corrugation region is fully described in copending U.S. patent application Ser. No. 08/538,706 (Attorney Docket 16380-38), the full disclosure of which has previously been incorporated herein by reference.

Figure 7:
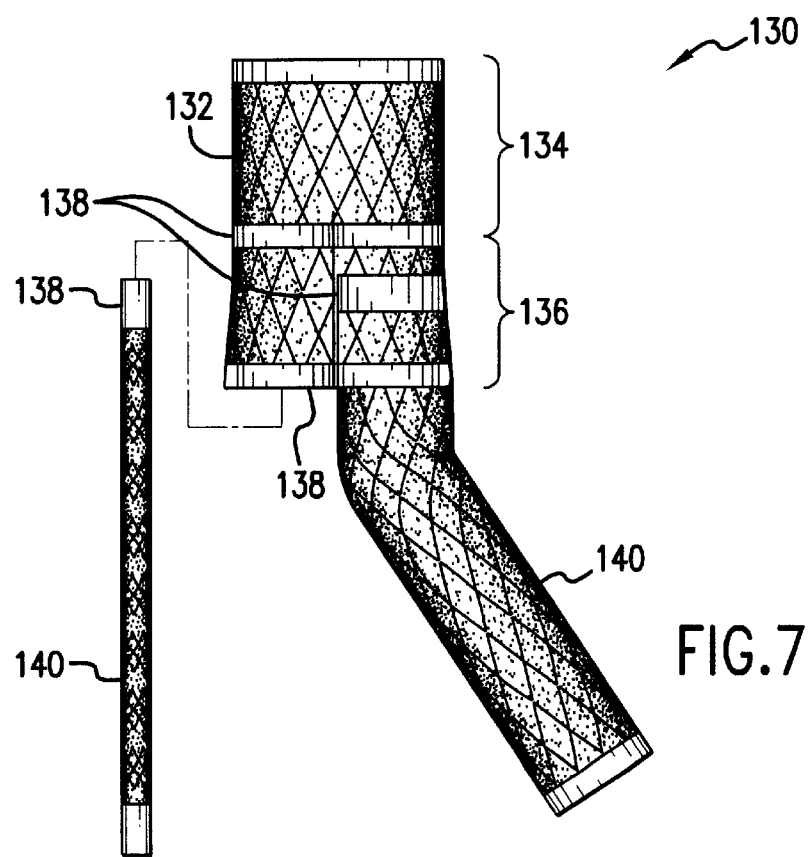
FIG. 7 is an exploded view of a branching endoluminal prosthesis assembled from position-indicating prosthetic modules having overlap indicators according to the principles of the present invention.

Referring now to FIG. 7, a modular position-indicating branched stent-graft 130 comprises a marked Y-connector 132 and marked branch modules 140. Marked Y-connector 132 includes a main body 134 and a septum 136 as described above. Overlap marker bands 138 provide a bright contrast under fluoroscopy, ultrasound, or other imaging modalities, to ensure that the marked Y-connector and marked branch modules overlap within a predetermined range. Were the overlap allowed to exceed that predetermined range, the branch prosthesis module would extend into the main body portion of the Y-connector module, where it is no longer supported by the septum frame, and where it might therefore fold over and block flow into either or both branches. Were the overlap insufficient, the branch and Y-connector modules may become separated, allowing blood to flow through a ruptured aneurysm.

In the embodiment shown, the overlap is within the range so long as the branch marker band image is between and separate from the marker bands of the septum. The use of an overlap-indicating delivery system to provide similar safety benefits was described in copending U.S. patent application Ser. No. 08/475,200 (Attorney Docket 16380-11-3), the full disclosure of which is incorporated herein by reference.

It is particularly advantageous to provide marker bands which are visible while the prosthetic modules are radially compressed for insertion and positioning, and which are also visible once the modules are fully expanded and interlocked, thereby allowing module positioning and verification of the assembled prosthesis. The preferred markers will therefore expand with the prosthesis, but will not add significant bulk so as to impede radial compression. Optionally, tantalum, platinum, gold, tin, or the like may be coated onto the frame in selected areas to provide a radio opaque marker. Alternatively, metal wire might be wrapped around selected portions of the frame or woven into the liner. Although such methods are fairly effective, they are generally labor-intensive, bulky, and do not provide the bright, continuous, clearly defined image which is desired.

In a particularly preferred embodiment, marker bands and other position-indicating elements may be applied directly to the flexible liner material as a radio opaque paste or paint. Such a paste may be prepared by mixing tantalum powder with a polyester in a suitable solvent, such as hexafluoro-2 propanol. This radiopaque paste may then be painted onto a woven Dacron™ or other suitable liner in the desired shapes. The relative proportions of the materials may be varied to provide the desired image density and adhesion qualities.

Figure 8:
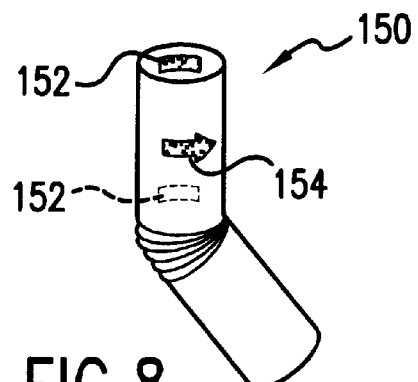
FIGS. 8–8B illustrate alternative embodiments of endoluminal prostheses having rotational markers, including both asymmetric elements and alignable elements at differing radial positions.

Referring now to FIG. 8, the angled prostheses of the present invention will often be formed with a bend at a specific rotational orientation. It is therefore highly advantageous to provide marking elements which provide an indication of the rotational orientation of the prosthesis to facilitate the alignment of the prosthetic bend with the bends of the body lumen system. Rotational-indicating angle prosthesis 150 includes alignable marker elements 152 and an asymmetric marker element 154.

The asymmetric element 154 indicates the general orientation of the prosthesis during positioning. The precise rotational alignment of the prosthesis is then provided by aligning the image of alignable elements 152 with the asymmetric element 154, these elements being situated at different axial positions about the tubular prosthesis. By first positioning the fluoroscopic, ultrasound, or other imaging mechanism in the proper orientation relative to the body lumen, and by then aligning the marker elements of the prosthesis relative to that orientation, very precise rotational alignment of the prosthesis can be achieved.

Figure 8A:
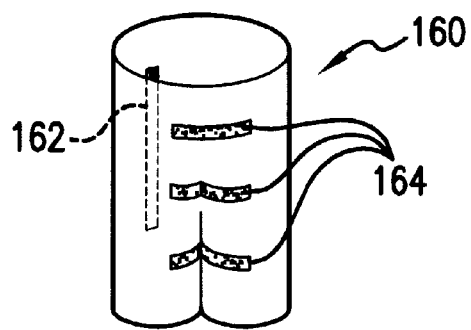
Figure 8B:
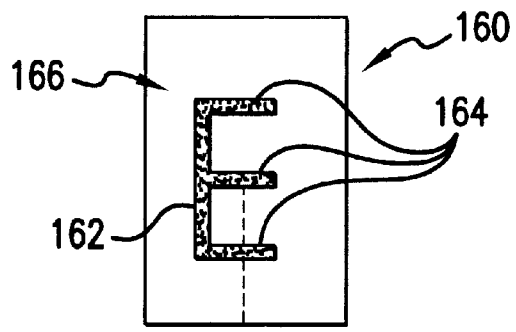

Referring now to FIGS. 8A–B, a rotational-indicating Y-connector module 160 includes a vertical marker bar 162 and horizontal alignment bars 164. These elements are again disposed at differing radial positions about the prosthesis, providing precise angular alignment of the prosthesis through alignment of the marker element images. In this embodiment, the marker elements align to form the asymmetric angular position indicator 166, here forming the letter "E".

Clearly, a wide variety of alternative rotational indicator markers might be used. Nonetheless, the combination of an asymmetric marker to prevent misalignment of the prosthesis by 180°, in combination with alignable elements at differing radial positions to provide precise angular alignment is preferred for prostheses which do not have an axial plane of symmetry.

Figure 9:
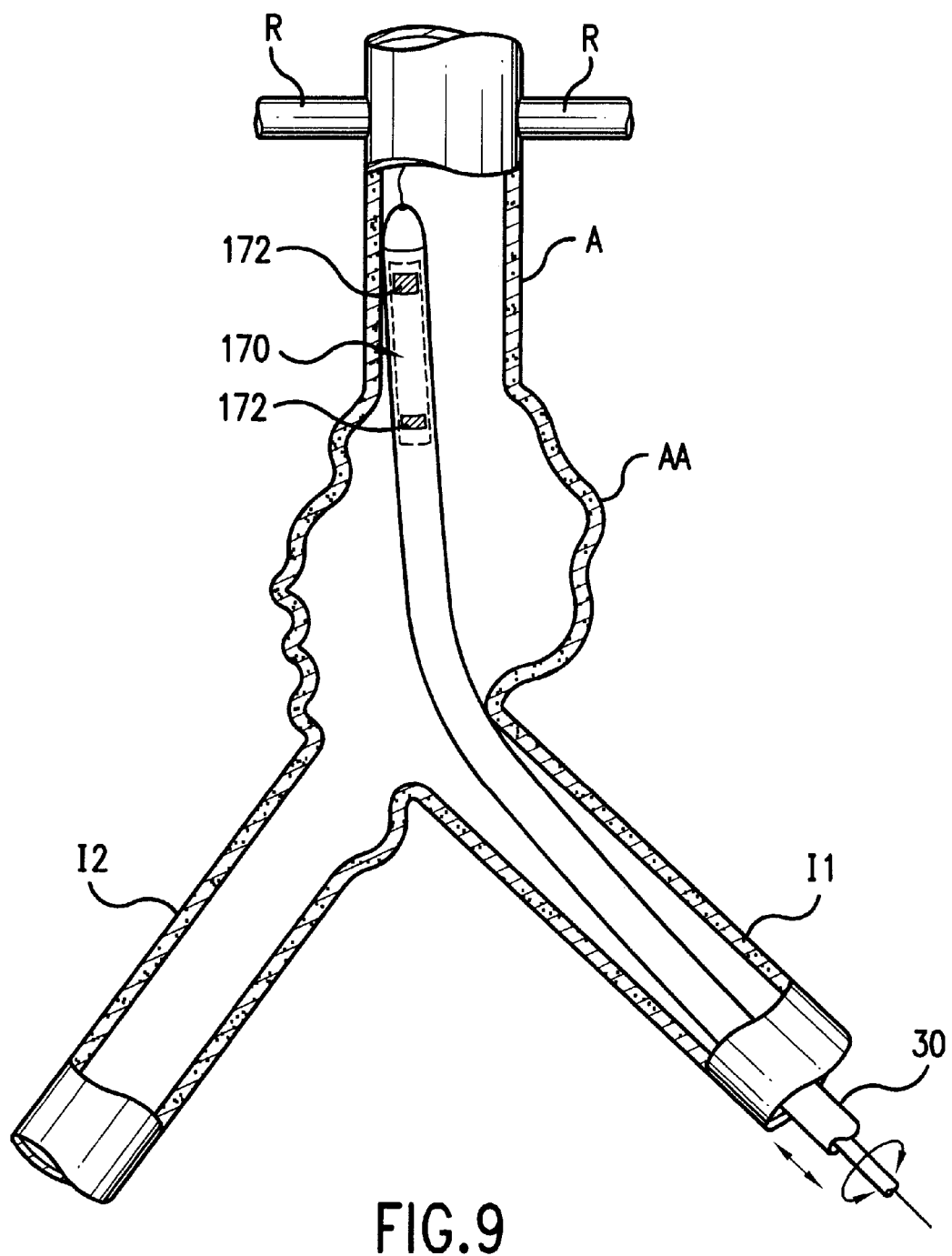
FIGS. 9–9C illustrate an exemplary method for assembling prosthetic modules into a branching endoluminal prosthesis in situ within a branching body lumen system, according to the principles of the present invention.
Figure 9A:
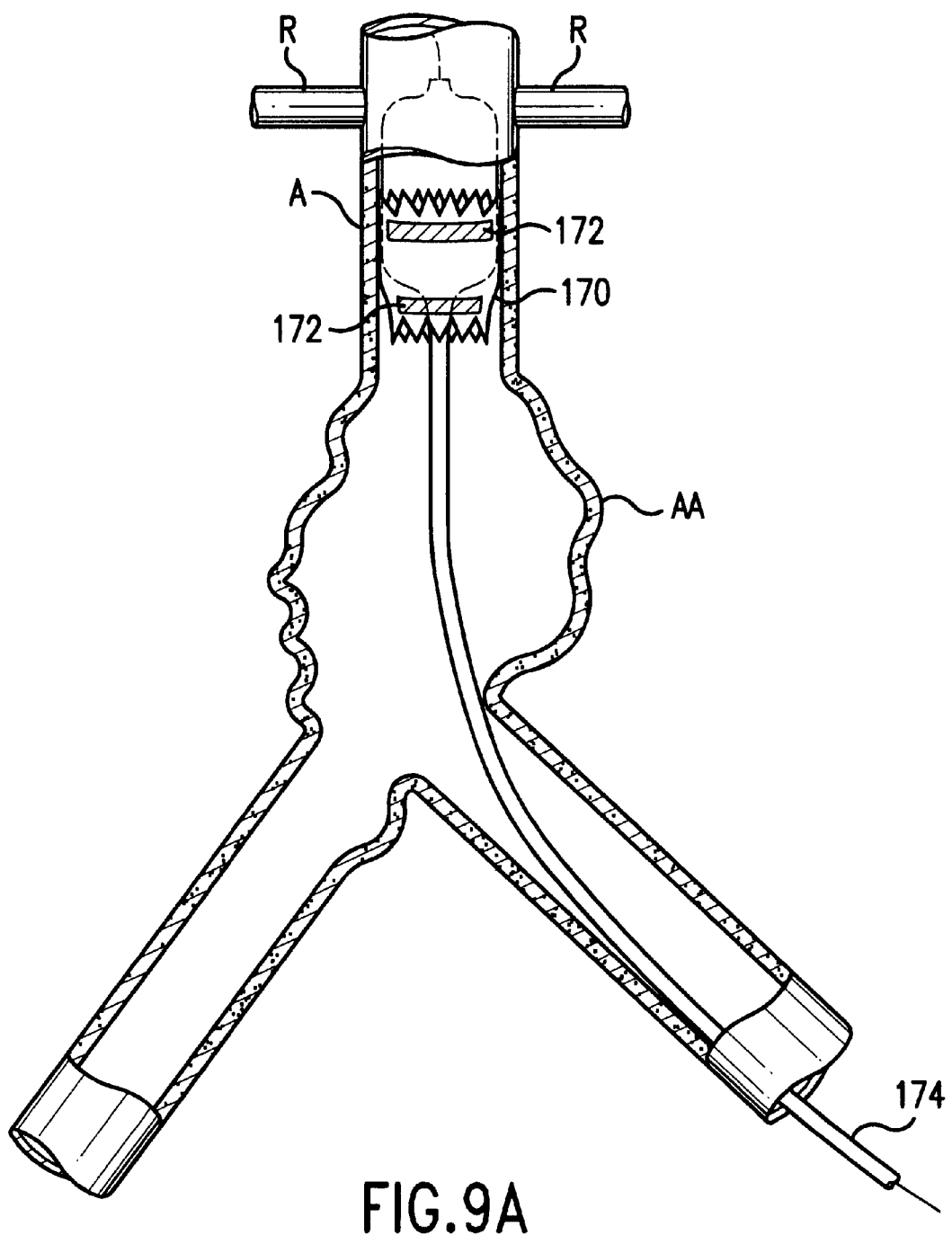
Figure 9B:
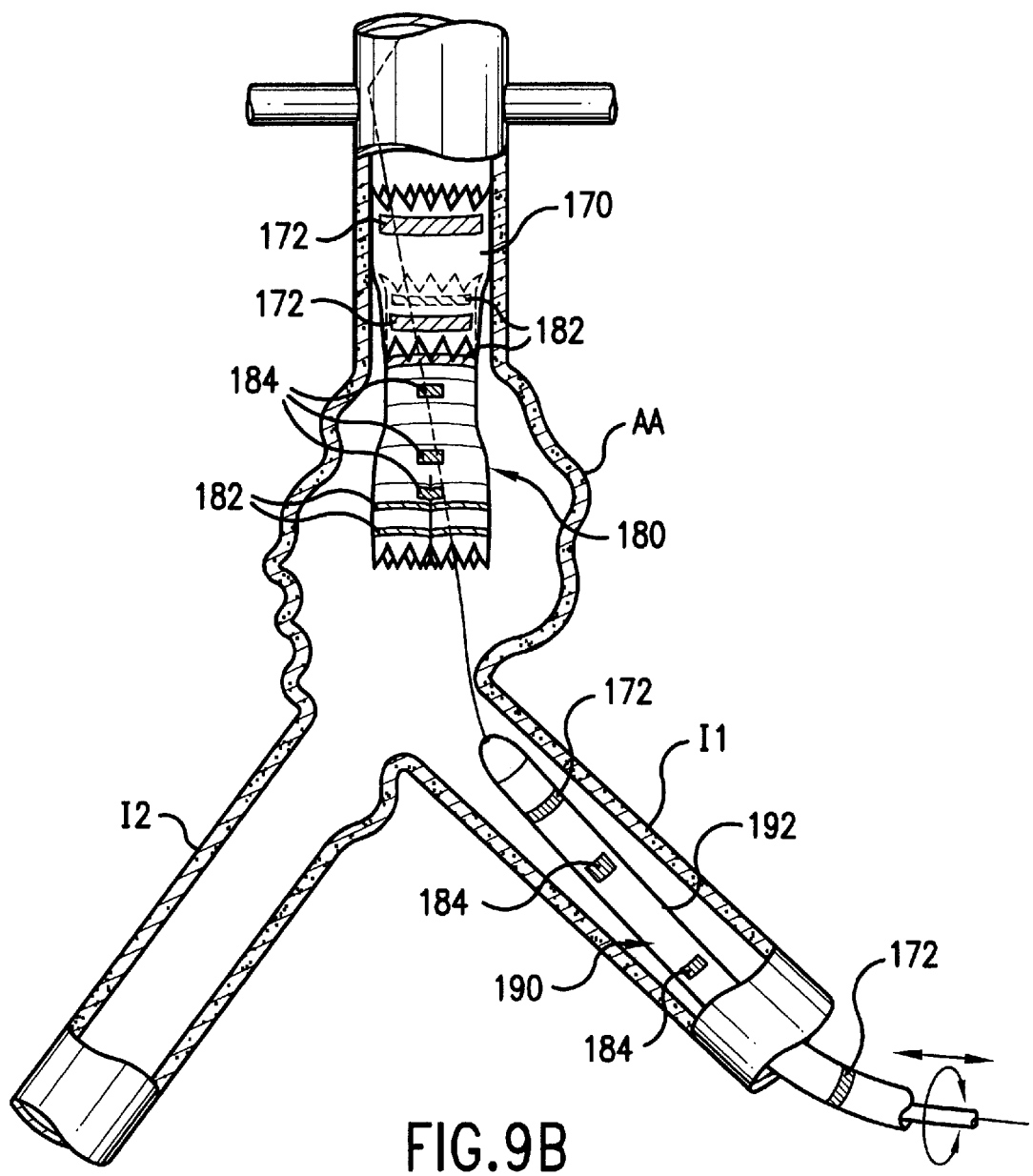
Figure 9C:
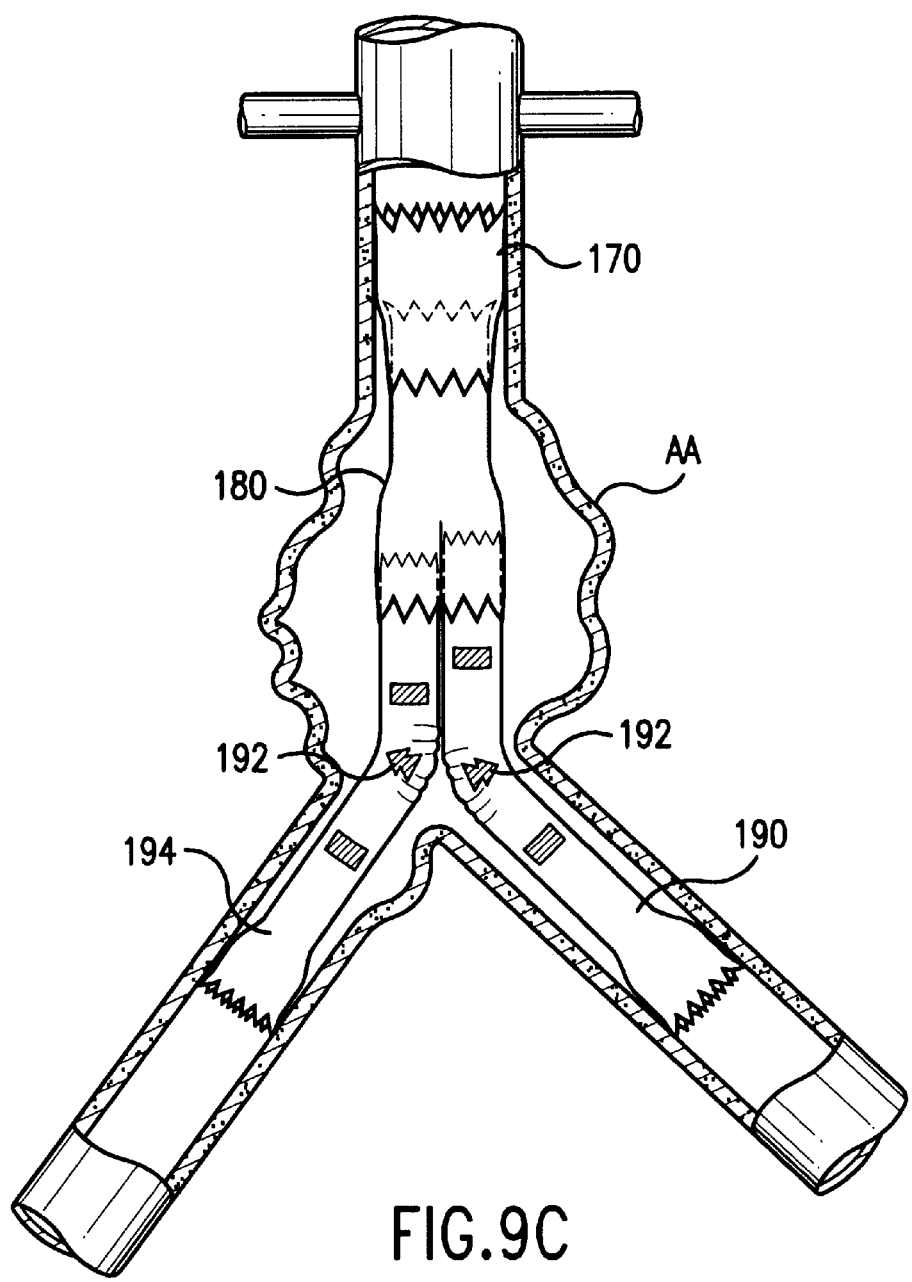

The in situ assembly of the modular bifurcated prostheses of the present invention may be understood with reference to FIGS. 9–9C. Abdominal aneurysm AA is located below the renal arteries R, and extends down into at least one of the iliac arteries I1, I2. A cuffed endoluminal prosthetic module 170 having marker bands 172 at either end is inserted with an inferior approach and positioned using delivery catheter 30. Marker bands 172 help to position cuffed module 170 at a target location below the renal arteries, with a majority of the prosthesis adjacent to the healthy luminal wall of the aorta A.

Once the module is at the target location, cuffed module 170 is expanded. Typically, the module expands resiliently as the delivery catheter cover is removed. Ideally, an expansible liner is then plastically expanded by balloon catheter 174 to match the prosthesis perimeter to that of the surrounding aorta, as shown in FIG. 9A, and as more fully explained in copending application Ser. No. 08/538,706 (Attorney Docket No. 16380-38).

Once the cuffed module is in place, position-indicating Y-connector module 180 is then inserted and positioned within the lower end of cuffed module 170. Overlap indicators 182 are positioned on either side of marker band 172 to ensure that the overlap is within the predetermined range. The prosthesis is rotated until alignable elements 184 are vertically aligned. As this Y-connector module is formed with symmetric branches, no asymmetric element is required. Alternatively, a Y-connector module having one integral branch might be used, in which case an asymmetrical element would prevent misalignment of the open bifurcated lumen. Otherwise, misalignment or crossing of the branches might seriously occlude flow through one or both branch lumens.

The overlapped interface ends of the cuffed module and the Y-connector module may optionally be "locked" together by plastically expanding the inner interface end with balloon catheter 174. Preferably, the outer interface end of the cuffed module includes a non-distensible liner to avoid stressing the body lumen, while the Y-connector interface end comprises a plastically expansible liner such as a partially oriented yarn. Such locking of the overlapped modules helps ensure that the joints remain fixed once proper positioning has been completed.

First angled branch prosthetic module 190 is next positioned within the septum of the Y-connector module 180. Marker band 172 is again positioned between the overlap indicators 182 (not shown in FIG. 9C for clarity), while the preset radial orientation of the branch angle bend is indicated by asymmetric element 192. The visibility of the various position-indicator markers prior to expansion of the prostheses can be seen to facilitate positioning of the prostheses using delivery catheter 30. Additionally, their continued visibility on the prosthetic modules helps to ensure continued alignment of the various modules as assembly proceeds.

Figure 10:
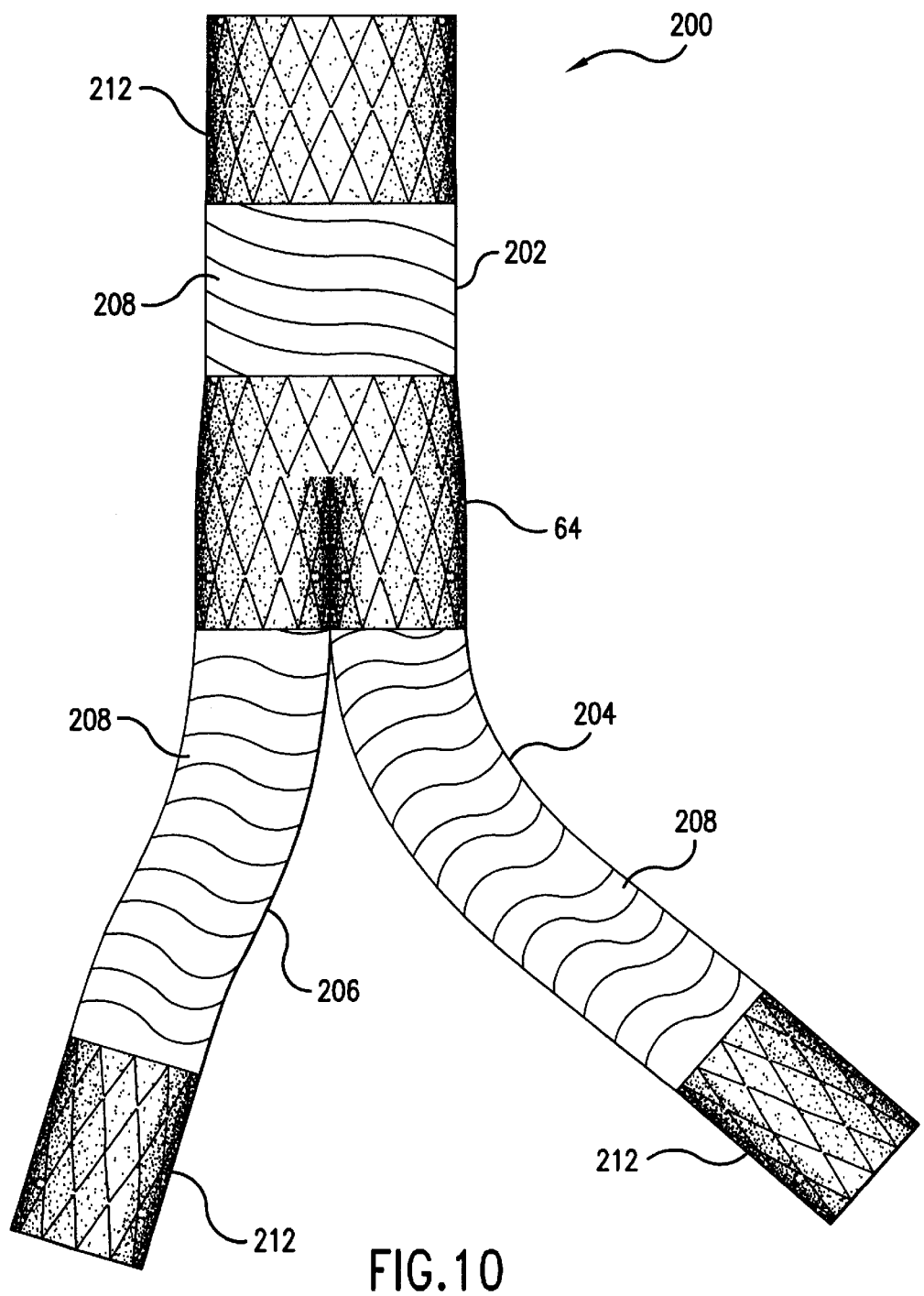
FIG. 10 illustrates an alternative branching endoluminal prosthesis assembled from prosthetic modules, including modules having highly flexible sections along which a liner is supported by helical windings, according to the principles of the present invention.

Referring now to FIG. 10, a highly flexible prosthesis is again assembled from a plurality of prosthetic modules, including Y-connector module 64, a flexible common lumen module 202, and first and second branch modules 204, 206. Each of flexible modules 202, 204, and 206 comprise a highly flexible section including a flexible liner material 208 which is supported by a frame comprising at least one spiral member 210. Such a spiral structure will hold the liner open radially, and will also provide some axial support, but will generally not substantially increase the axial stiffness, allowing the prosthesis to adapt to the highly tortuous branching paths which often occur with aneurysms. Preferably, one or two spiral members are used to maximize axial flexibility. Where two spiral members are included, they may be counterwound.

The ends 212 of flexible modules 202, 204, and 206 opposite the Y-connector module preferably include anchoring frames, ideally comprising resilient cuffs to seal against the surrounding lumenal wall, as described above. Ring frame sections may also be incorporated into the ends of the flexible modules which engage the Y-connector structure to provide sealing and prevent relative movement of the modules. Finally, it should be recognized that the Y-connector and the common lumen module and/or one of the branch modules may be produced as a single unit, so that only a single branch is a assembled in situ. In fact, such spirally supported intermediate flexible prosthetic sections, for use between anchoring frame sections, need not be limited to modular prostheses.

While the foregoing has been described in some detail, for purposes of clarity and understanding, certain changes and modifications will be obvious to those of skill in the art. Thus, the scope of the present invention is limited solely by the appended claims.

What is claimed is:

1. An endoluminal support device comprising:

a radially-expandable, bifurcated support, the support including:

a first support portion, and a second support portion including a first lobe and a second lobe, and a longitudinal isthmus between the first lobe and the second lobe, the first and second lobes having smaller diameters than the first portion; and a liner coupled to the radially-expandable, bifurcated support, wherein the endoluminal support device has an uninterrupted cross-section over its entire length.

2. The endoluminal support device of claim 1, wherein the liner is coupled to an interior side of the radially-expandable, bifurcated support.

3. The endoluminal support device of claim 1, wherein the liner is coupled to an exterior side of the radially-expandable, bifurcated support.

4. The endoluminal support device of claim 1, wherein each of the first and second lobes is adapted to receive a branch support.

5. The endoluminal support device of claim 1, wherein the radially-expandable, bifurcated support is formed of a plurality of ring members.

6. The endoluminal support device of claim 5, wherein the ring members are attached to each other by stitching.

7. The endoluminal support device of claim 5, wherein the ring members are self expanding.

8. The endoluminal support device of claim 5, wherein the ring members are formed of stainless steel.

9. The endoluminal support device of claim 5, wherein the ring members are formed of Nitinol.

10. The endoluminal support device of claim 5, wherein the ring members are independent.

11. An endoluminal support device comprising:

a plurality of independent, expandable ring members forming a bifurcated vascular support structure;

the bifurcated vascular support structure having a first longitudinally-oriented portion with a generally circular cross-section and a second portion with at least one longitudinal indentation; and a liner coupled to the support structure, wherein the endoluminal support device has an uninterrupted cross-section over its entire length.

12. The endoluminal support device of claim 11, wherein the second portion includes two lobes.

13. The endoluminal support device of claim 12, wherein each of the two lobes is adapted to receive a branch support.

14. The endoluminal support device of claim 11, wherein the ring members are self-expanding.

15. The endoluminal support device of claim 11, wherein the ring members are formed of stainless steel.

16. The endoluminal support device of claim 11, wherein the ring members are formed of Nitinol.

17. The endoluminal support device of claim 11, wherein the liner is coupled to an interior side of the support structure.

18. The endoluminal support device of claim 11, wherein the liner is coupled to an exterior side of the support structure.

19. The endoluminal support device of claim 17, further comprising a bifurcated liner coupled to the support structure.

20. The endoluminal support device of claim 11, wherein the ring members are attached to each other by stitching.

21. The endoluminal support device of claim 11, wherein the second portion includes at least two longitudinal indentations.

22. A branching endovascular prosthesis comprising:
   a radially expandable support, the support including:
      a distal support portion comprising at least one expandable circumferential portion, and
      a proximal support portion including a first lobe and a second lobe separated from the first lobe by an isthmus, and
   a bifurcated liner coupled to the distal support portion and to the proximal support portion,
   wherein the branching endovascular prosthesis has an uninterrupted cross-section over its entire length.

23. The prosthesis of claim 22, wherein the bifurcated liner is coupled an interior side of the distal support portion and to an interior side of the proximal support portion.

24. The prosthesis of claim 22, wherein the bifurcated liner is coupled an exterior side of the distal support portion and to an exterior side of the proximal support portion.

25. The prosthesis of claim 22, wherein the support is formed of a plurality of ring members.

26. The prosthesis of claim 25, wherein the ring members are attached to each other by stitching.

27. The prosthesis of claim 25, wherein the ring members are independent.

28. The endoluminal support device of claim 25, wherein the ring members are formed of stainless steel.

29. The prosthesis of claim 25, wherein the ring members are formed of Nitinol.

30. The prosthesis of claim 22, wherein the prosthesis is self explanding.

31. A branching endovascular prosthesis comprising:
   a distal support portion comprising at least one radially expandable portion;
   a proximal support portion coupled to the distal support portion,
   the proximal support portion including a first radially expandable lobe and a second radially expandable lobe separated from the first lobe by an isthmus; and
   a bifurcated liner coupled to the distal support portion and to the proximal support portion,
   wherein the branching endovascular prosthesis has an uninterrupted cross-section over its entire length.

32. The prosthesis of claim 31, wherein the bifurcated liner is coupled to an interior side of the distal support portion and to an interior side of the proximal support portion.

33. The prosthesis of claim 31, wherein the bifurcated liner is coupled an exterior side of the distal support portion and to an exterior side of the proximal support portion.

34. The prosthesis of claim 31, wherein the prosthesis is formed of a plurality of ring members.

35. The prosthesis of claim 34, wherein the ring members are attached to each other by stitching.

36. The prosthesis of claim 34, wherein the ring members are self explanding.

37. The prosthesis of claim 34, wherein the ring members are independent.

38. The prosthesis of claim 34, wherein the ring members are formed of stainless steel.

39. The prosthesis of claim 34, wherein the ring members are formed of Nitinol.

40. An endoluminal support device comprising:
   a plurality of independent ring members forming an expandable bifurcated vascular support structure,
   each ring member having a circumferentially repeating diamond pattern, and
   the bifurcated vascular support structure having an uninterrupted cross-section over its entire length; and
   a bifurcated liner coupled to the bifurcated vascular support structure.

41. The endoluminal support device of claim 40, wherein the expandable bifurcated vascular support structure includes two lobes.

42. The endoluminal support device of claim 41, wherein each of the two lobes is adapted to receive a branch support.

43. The endoluminal support device of claim 40, wherein the ring members are self-expanding.

44. The endoluminal support device of claim 40, wherein the ring members are formed of stainless steel.

45. The endoluminal support device of claim 40, wherein the liner is coupled to an interior side of the endoluminal support device.

46. The endoluminal support device of claim 45, wherein the liner is bifurcated.

47. The endoluminal support device of claim 40, wherein the ring members are attached to each other by stitching.

48. The endoluminal support device of claim 40, wherein the ring members are formed of Nitinol.

49. A branching endoluminal prosthesis comprising:
   a liner and a radially expandable support coupled to said liner;
   wherein said liner comprises:
      a main body having a proximal portion and a distal portion, said proximal portion including a main lumen, and said distal portion including a first branch having a first lumen extending to a first distal end, and a second branch having a second lumen extending to a second distal end, the first and second branch lumens being in communication with the main lumen and extending through said distal portion to define a bifurcation extending to said first and second distal ends; and
   wherein said support comprises:
      a distal support portion disposed over said distal portion of said main body, said distal support portion comprising at least one expandable circumferential portion defining a first lobe supporting said first branch, a second lobe supporting said second branch, and opposed indentations to support and separate said first and second branches,
   wherein said branching endoluminal prosthesis has an uninterrupted cross-section over its entire length.

50. The branching endoluminal prosthesis of claim 49 wherein said support further comprises a, an expandable proximal circumferential portion supporting said proximal portion of said main body.

51. The branching endoluminal prosthesis of claim 49 further comprising an attachment mechanism which couples said distal support to said distal portion of said main body of said liner.

52. The branching endoluminal prosthesis of claim 51 wherein said attachment mechanism attaches said first lobe and a portion of each indentation to the first branch.

53. The branching endoluminal prosthesis of claim 52 wherein said attachment mechanism attaches said second lobe and a portion of each indentation to the second branch.

54. The branching endoluminal prosthesis of claim 49 wherein said support comprises a plurality of independent ring members.

* * * * *